US00PP15022P2

(12) United States Plant Patent
Talmadge

(10) Patent No.: US PP15,022 P2
(45) Date of Patent: Jul. 20, 2004

(54) DIASCIA PLANT NAMED 'PINKWSM'

(50) Latin Name: *Diascia×hybrida*
Varietal Denomination: Pinkwsm

(75) Inventor: Paul A. Talmadge, Orcutt, CA (US)

(73) Assignee: Pan American Seed, a divsion of Ball Horticultural Company, West Chicago, IL (US)

( * ) Notice: Subject to any disclaimer, the term of this patent is extended or adjusted under 35 U.S.C. 154(b) by 185 days.

(21) Appl. No.: 10/228,459

(22) Filed: Aug. 27, 2002

(51) Int. Cl.[7] ..... A01H 5/00
(52) U.S. Cl. ..... Plt./263
(58) Field of Search ..... Plt./263

(56) References Cited

PUBLICATIONS

COPF News, October 2001, http://www.copf.cu/auwa/pdf/10–01.pdf pp. 1–11, p. 5.*

UPOV–ROM, Canada Plant Breeders' Right Lit, PBR 01–2602, Feb. 8, 2001.*

* cited by examiner

*Primary Examiner*—Anne Marie Grunberg
(74) *Attorney, Agent, or Firm*—C. A. Whealy

(57) ABSTRACT

A new and distinct cultivar of Diascia plant named 'Pinkwsm', characterized by its upright, outwardly spreading, and compact plant habit; freely and continuous branching; and numerous red purple-colored flowers.

1 Drawing Sheet

Botanical classification/cultivar designation: *Diascia×hybrida* cultivar Pinkwsm.

BACKGROUND OF THE INVENTION

The present Invention relates to a new and distinct cultivar of Diascia plant, botanically known as *Diascia×hybrida*, and hereinafter referred to by the cultivar name Pinkwsm.

The new Diascia is a product of a planned breeding program conducted by the Inventor in Guadalupe, Calif. The objective of the breeding program is to create new Diascias with numerous flowers with attractive coloration and good garden performance.

The new Diascia originated from a cross made by the Inventor during the summer of 1998 of the *Diascia×hybrida* cultivar Ruby Fields, not patented, as the female, or seed parent, with the *Diascia×hybrida* cultivar Red Start, not patented, as the male, or pollen parent. The new Diascia was selected as a single plant from the resulting progeny by the Inventor during the summer of 1998, in Guadalupe, Calif. on the basis of its attractive flower color.

Asexual reproduction of the new cultivar by cuttings taken in Guadalupe, Calif. since the summer of 1998 has shown that the unique features of this new Diascia are stable and reproduced true to type in successive generations.

SUMMARY OF THE INVENTION

Plants of the cultivar Pinkwsm have not been observed under all possible environmental conditions. The phenotype may vary somewhat with variations in environment such as temperature and light intensity without, however, any variance in genotype.

The following traits have been repeatedly observed and are determined to be the unique characteristics of 'Pinkwsm'. These characteristics in combination distinguish 'Pinkwsm' as a new and distinct Diascia cultivar:

1. Upright and outwardly spreading plant habit.
2. Freely branching habit.

3. Freely and continuous flowering habit.
4. Red purple-colored flowers.

Plants of the new Diascia are most similar to plants of the parent cultivars. Compared to plants of the female parent, the cultivar Ruby Fields, plants of the new Diascia are more outwardly spreading, are more vigorous, and flower more continuously. In addition, plants of the new Diascia do not set seed whereas plants of the cultivar Ruby Fields set seed. Compared to plants of the male parent, the cultivar Red Start, plants of the new Diascia are more outwardly spreading, are more vigorous, and flower more continuously.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs differ slightly from the color values cited in the detailed botanical description which accurately describe the colors of the new Diascia.

The photograph at the top of the sheet comprises a side perspective view of three typical flowering plants of 'Pinkwsm' grown in a 20-cm container.

The photograph at the bottom of the sheet comprises a close-up view of typical flowering stems, developing flowers, fully opened flowers, and the upper and lower surfaces of typical leaves of 'Pinkwsm'.

DETAILED BOTANICAL DESCRIPTION

The aforementioned photographs and following observations and measurements describe plants grown in Encinitas, Calif., in an outdoor nursery under full sunlight conditions during the late winter and early spring with day temperatures averaging 24° C. and night temperatures averaging 12° C. Plants were grown for 16 weeks in 19-cm containers with three plants per container and were pinched one time. Color references are made to The Royal Horticultural Society Colour Chart, 1995 Edition, except where general terms of ordinary dictionary significance are used.

Botanical classification: *Diascia×hybrida* cultivar Pinkwsm.

Parentage:

*Female parent.*—*Diascia×hybrida* cultivar Ruby Fields, not patented.

*Male parent.*—*Diascia×hybrida* cultivar Red Start, not patented.

Propagation:

*Type.*—By cuttings.

*Time to initiate roots.*—About 6 to 8 days at 20° C.

*Time to produce a rooted young plant.*—About 18 to 22 days at 20° C.

*Root description.*—Fine and fibrous; white in color.

*Rooting habit.*—Freely branching.

Plant description:

*Form/growth habit.*—Upright, outwardly spreading and compact plant habit. Freely branching with more than 45 lateral branches per plant. Moderately vigorous growth habit.

*Plant height.*—About 19 cm.

*Plant diameter.*—Single plant: About 26 cm. Three plants: About 48 cm.

*Lateral branches.*—Aspect: Initially upright, then outwardly spreading. Length: About 28 cm. Diameter: About 1.5 mm. Internode length: About 2.5 cm. Texture: Smooth, glabrous. Color: 144A.

*Foliage description.*—Arrangement: Opposite; simple. Quantity per lateral branch: About 14. Length: About 2 cm. Width: About 1.8 cm. Shape: Ovate with cordate tendencies. Apex: Broadly acute. Base: Cordate. Margin: Slightly serrate. Texture: Smooth, glabrous. Venation pattern: Pinnate. Color: Young and mature foliage, upper surface: 146A. Young and mature foliage, lower surface: 147C. Venation, upper surface: 146B. Venation, lower surface: 147C. Petiole length: About 5 mm. Petiole diameter: About 2 mm. Petiole color: 146B.

Flower description:

*Flower type and habit.*—Solitary axillary flowers; zygomorphic.

*Five modified petals fused at base.*—Two upper (banner) petals, two lateral petals and one larger lower lip petal. Flowers not persistent. Very freely flowering; typically about 15 buds and flowers per lateral branch. Flowers face mostly outward.

*Natural flowering season.*—Plants typically flower from March through June in the Northern Hemisphere; flowering continuous during this period.

*Flower longevity on the plant.*—About 3 to 4 days.

*Fragrance.*—Not detected.

*Flower size.*—Height: About 1.7 cm. Width: About 1.4 cm. Depth (height): About 8 mm.

*Flower buds* (*showing color*).—Length: About 4 mm. Diameter: About 4.5 mm. Shape: Oval. Color: 70C to 70D.

*Petals.*—Quantity/arrangement: Five modified petals fused at base: two upper (banner) petals, two lateral petals and one larger lower lip petal. Base of banner petals with indented yellow eyespots; lower surfaces of lateral petals modified into nectar spurs; and lower lip petal convex forming horizontal insect landing platform. Length: Banner petals: About 5 mm. Lateral petals: About 5 mm. Lower lip petal: About 9 mm. Width: Banner petals: About 5 mm. Lateral petals: About 7 mm. Lower lip petal: About 1.1 cm. Lateral petal spur: Length: About 8 mm. Diameter, at petal attachment: About 2 mm. Shape, all petals: Roughly spatulate. Apex, all petals: Rounded. Margin, all petals: Entire. Texture, all petals: Smooth, velvety. Color, all petals: Upper surface, when opening: 64D. Lower surface, when opening: 70D. Upper surface, fully opened: 58C; at base of petals, 64B; color does not fade with subsequent development. Lower surface, fully opened: 58D. Nectar spurs: 59D. Eyespots on banner petals: 5A.

*Sepals.*—Arrangement/appearance: Single whorl of five sepals fused at base; star-shaped. Length: About 3 mm. Diameter: About 1 mm. Shape: Elliptic. Apex: Acute. Margin: Entire. Texture, upper and lower surfaces: Smooth, glabrous. Color, immature and mature: Upper surface: 146B. Lower surface: 146A.

*Peduncles.*—Length: About 1.2 cm. Width: Less than 1 mm. Angle: About 45° from the stem. Strength: Moderately strong; slender. Texture: Smooth. Color: 144B.

*Reproductive organs.*—Stamens: Quantity per flower: Four. Anther shape: Ovoid. Anther length: Less than 1 mm. Anther color: 7A. Pollen amount: Scarce. Pollen color: 7A. Pistils: Quantity per flower: One. Pistil length: About 4 mm. Style length: About 2 mm. Style color: 144D. Stigma shape: Rounded. Stigma color: 144D. Ovary color: 144C.

*Seed/fruit.*—Seed nor fruit production has not been observed.

Disease/pest resistance: Plants of the new Diascia have not been noted to be resistant to pathogens or pests common to Diascia.

Temperature tolerance: Plants of the new Diascia have been observed to tolerate temperatures from 0 to 32° C.

It is claimed:

1. A new and distinct cultivar of Diascia plant named 'Pinkwsm', as illustrated and described.

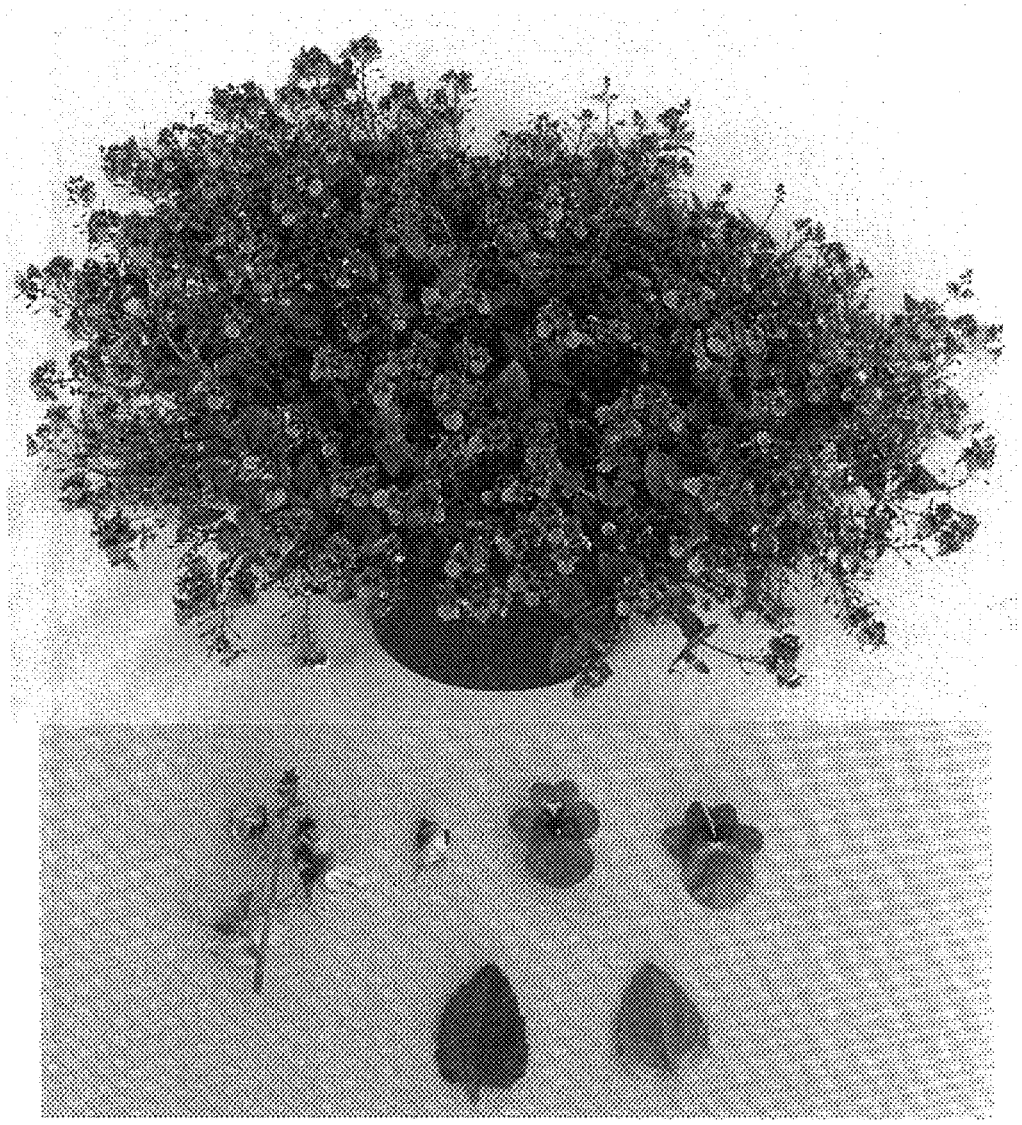

* * * * *